(12) United States Patent
Hakky et al.

(10) Patent No.: US 7,264,609 B2
(45) Date of Patent: Sep. 4, 2007

(54) INDWELLING URINARY CATHETER

(76) Inventors: Said I. Hakky, 8547 Merrimoor Blvd. East, Largo, FL (US) 33777-3145; A-Hamid Hakki, 1508 Sturbridge Ct., Dunedin, FL (US) 34698

( * ) Notice: Subject to any disclaimer, the term of this patent is extended or adjusted under 35 U.S.C. 154(b) by 252 days.

(21) Appl. No.: 10/701,515

(22) Filed: Nov. 6, 2003

(65) Prior Publication Data

US 2005/0101941 A1 May 12, 2005

(51) Int. Cl.
*A61M 29/00* (2006.01)
(52) U.S. Cl. .................. 604/107; 604/99.02; 604/907; 604/908; 604/912; 604/915
(58) Field of Classification Search .............. 604/907, 604/908, 912, 915–921, 540, 544, 96.01, 604/99.02, 103–107
See application file for complete search history.

(56) References Cited

U.S. PATENT DOCUMENTS

| | | | |
|---|---|---|---|
| 318,535 A | 5/1885 | Bihler | |
| 2,616,429 A | 11/1952 | Merenlender | |
| 2,649,092 A | 8/1953 | Wallace | |
| 2,854,983 A * | 10/1958 | Baskin | 604/103.11 |
| 3,108,595 A | 10/1963 | Overment | |
| 3,397,699 A | 8/1968 | Kohl | |
| 3,472,230 A | 10/1969 | Fogarty | |
| 3,799,172 A | 3/1974 | Szpur | |
| 3,815,608 A * | 6/1974 | Spinosa et al. | 604/105 |
| 3,938,530 A | 2/1976 | Santomieri | |
| 4,018,231 A * | 4/1977 | Wallace | 128/207.15 |
| 4,154,242 A * | 5/1979 | Termanini | 604/105 |
| 4,168,699 A | 9/1979 | Hauser | |
| 4,292,974 A * | 10/1981 | Fogarty et al. | 606/194 |
| 4,335,723 A | 6/1982 | Patel | |
| 4,349,029 A | 9/1982 | Mott | |
| 4,575,371 A | 3/1986 | Nordqvist et al. | |
| 4,655,745 A * | 4/1987 | Corbett | 604/540 |
| 4,781,682 A | 11/1988 | Patel | |
| 4,787,892 A * | 11/1988 | Rosenberg | 604/170.02 |
| 4,813,935 A | 3/1989 | Haber et al. | |
| 4,861,337 A | 8/1989 | George | |
| 4,921,484 A | 5/1990 | Hillstead | |
| 5,041,093 A | 8/1991 | Chu | |
| 5,203,773 A | 4/1993 | Green | |
| 5,421,832 A | 6/1995 | Lefebvre | |
| 5,702,365 A | 12/1997 | King | |
| 5,749,852 A * | 5/1998 | Schwab et al. | 604/103.01 |

(Continued)

*Primary Examiner*—Tatyana Zalukaeva
*Assistant Examiner*—Michael G. Bogart
(74) *Attorney, Agent, or Firm*—Rosenberg, Klein & Lee

(57) ABSTRACT

A self-retaining catheter that eliminates the problem of residual urine and also of bladder wall irritation caused by continuous contact with a spherical retention balloon which does not rely on a stylet for placement. The system may use an internal control wire that reversibly foreshortens the proximal end of the catheter thus radially displacing longitudinal strips defined in the proximal catheter to form retention wings. Alternatively, a balloon situated between the longitudinal strips is inflated to force open the retention wings once inside the urinary bladder. Radial displacement of the retention wings widens the spaces between the longitudinal strips, these spaces constituting the drainage apertures which permit complete emptying of the urinary bladder. The radially displaced retention wings abut the bladder wall in a non-continuous manner thereby reducing the area of bladder-catheter contact and further reducing bladder wall irritation.

8 Claims, 4 Drawing Sheets

U.S. PATENT DOCUMENTS

| | | |
|---|---|---|
| 5,857,464 A | 1/1999 | Desai |
| 5,976,068 A * | 11/1999 | Hakky et al. ................. 600/29 |
| 6,052,612 A | 4/2000 | Desai |
| 6,096,103 A | 8/2000 | Hubbard et al. |
| 6,270,490 B1 | 8/2001 | Hahnen |
| 6,283,940 B1 * | 9/2001 | Mulholland ............... 604/96.01 |
| 6,638,247 B1 * | 10/2003 | Selmon et al. .............. 604/104 |
| 2001/0049494 A1 | 12/2001 | Liu |
| 2002/0143292 A1 | 10/2002 | Flinchbaugh |
| 2005/0065468 A1 * | 3/2005 | Goebel .................... 604/96.01 |

* cited by examiner

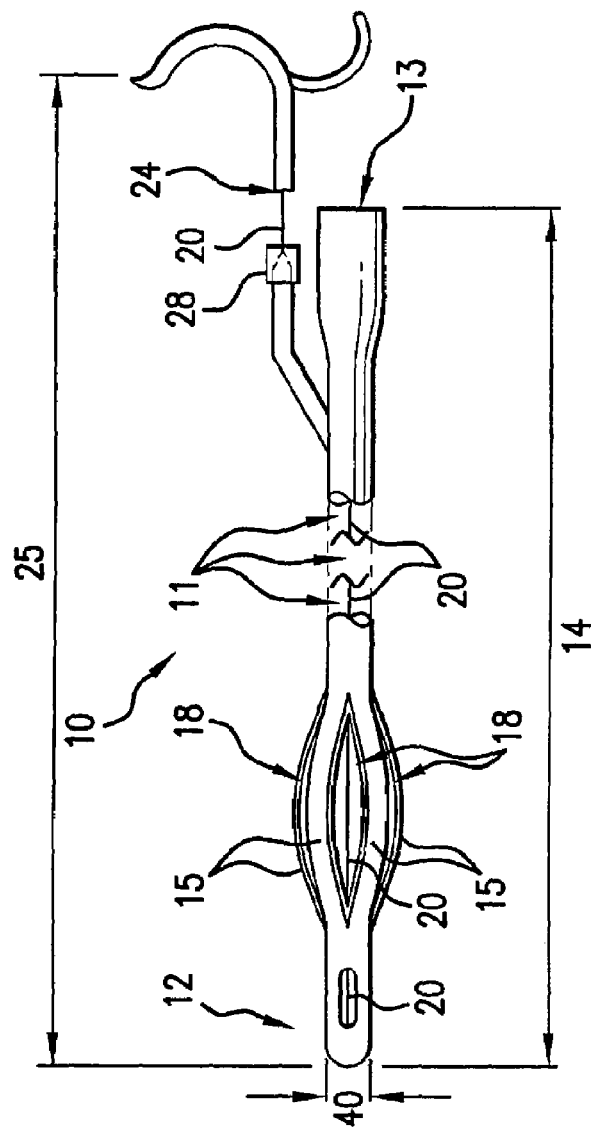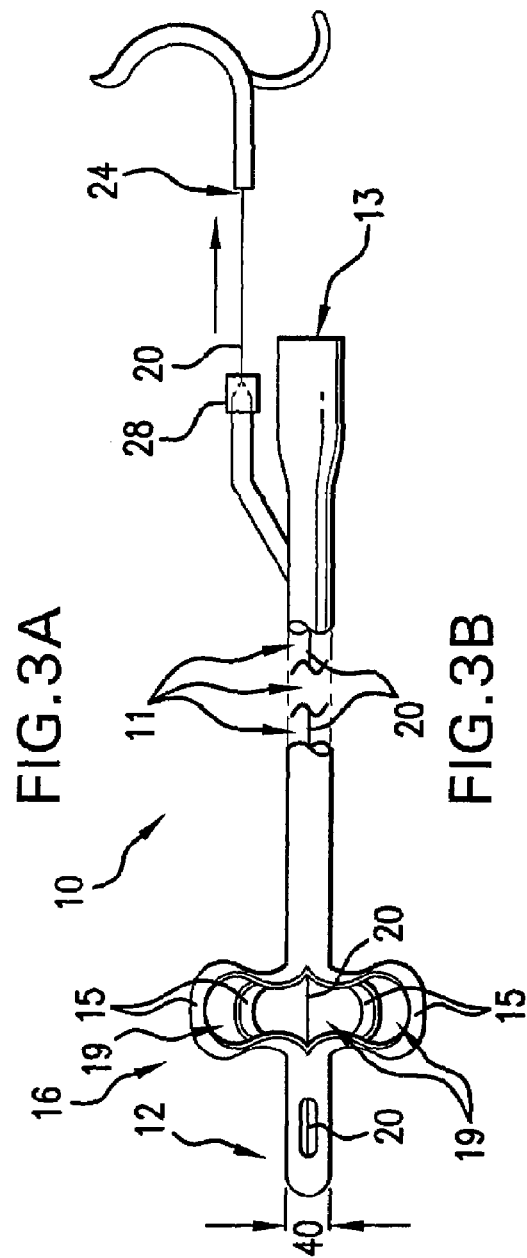
FIG.3A
FIG.3B

INDWELLING URINARY CATHETER

BACKGROUND OF THE INVENTION

1. Field of the Invention

This invention relates generally to the field of surgical devices, and, more particularly, to an indwelling catheter for draining the urinary bladder, with the proximal part of the catheter being self-retaining in a manner that minimizes bladder irritation and leaves essentially no residual urine in the bladder.

2. Prior Art

A urinary bladder drainage tube is used in certain patients who have had major surgery and/or trauma, or in any patient unable to urinate. There are many causes of an inability to urinate, these causes differing with age and sex. For example, a small child may not be able to urinate because of some congenital abnormality that obstructs the bladder neck or urethra. In females, inability to urinate occurs in neurological diseases, or after major abdominal or pelvic surgery.

It is often desirable to drain the bladder continuously after major surgery or trauma, at least for the purposes of monitoring renal function by measuring the hourly urine output. It is desirable to continuously drain the bladder by an indwelling urinary catheter in those medical conditions in which the measurement of hourly urine output is important for the timely and appropriate care and well being of the patient.

It is further important to drain the bladder by an indwelling urinary catheter after prostate or bladder surgery. Diverting the urine and blood promotes healing and helps to prevent blood clots from accumulating in the bladder, thus potentially causing more bleeding and severe pain.

Continuous bladder irrigation is used following certain bladder or prostate surgeries. This is achieved by instilling fluid continuously into the bladder and simultaneously draining the bladder using a type of urinary catheter called a three-way catheter. One port serves as a fluid injection port into the bladder, while the second port is for continuous drainage of the bladder contents into a urine collection bag. The third port incorporates a valve mechanism by which the catheter balloon is reversibly inflated once positioned inside the bladder to keep the tip of the indwelling urinary catheter in place.

In certain patients, the bladder must be drained for many years, as in some debilitated patients, or those with neurological or spinal cord lesions. If the bladder is not adequately drained the pressure in the bladder increases and the pressure likewise increases in the ureters and kidneys, causing the kidneys to become obstructed. Unrelieved bilateral kidney obstruction may lead to renal failure within a few weeks. Therefore, the use of an indwelling urinary catheter is quite important, and can be life saving both in acute and chronic or long-term settings.

There are some serious drawbacks to the standard indwelling urinary catheters now available. The widely-used Foley catheter has a retention balloon that is inflated when positioned inside the bladder and which rests on the most sensitive areas of the bladder, the trigone and bladder neck areas. The size of this retention balloon varies between 5 and 30 cc's and the general practice now is to inflate the catheter balloon with 10 to 30 ml's of water. The weight of the Foley catheter balloon when filled with water ranges between 10 and 30 grams. This weight often causes pain and bladder irritation, generally known among urologists to provoke very painful bladder spasms.

In addition to its weight, the balloon is situated below the drainage opening of the Foley catheter, so residual urine inevitably collects in the bladder around the balloon. The amount of residual urine that collects around the balloon averages between 3 and 10 mls. The presence of residual urine promotes infection and is a further source of bladder irritation. Furthermore, in rare instances, the balloon may be inadvertently inflated inside of the urethra, causing trauma to the urethra and resulting thereby in pain, bleeding and possible stricture formation within the urethra.

Pre-grant publication 2002/0143292 is directed to a conformable balloonless catheter system, an indwelling catheter with a proximal end that includes a retention portion made to expand without having to be inflated. One of the preferred embodiments allows for at least one slit on an upper side of the catheter tube and a head member that when pulled down by a stylette moving longitudinally inside the catheter causes a bulged wing portion that holds the catheter safely and painlessly within the bladder. As seen in FIGS. 11-14, traction on the stylette 50 causes the slit walls 68 to move radially as the proximal tip is pulled distally, thereby causing the catheter tip to assume a mushroom-type retention form while providing apertures for the drainage of urine. This is a complex catheter system that uses a stylet introducer with a a magnetic cycling valve and a screwing mechanism to open the retaining element. The use of a stylet to introduce the catheter into the urinary tract and bladder is dangerous and potentially traumatizing. The urethra is S-shaped when the penis is flaccid and becomes L-shaped when the penis is stretched or when erect; using a straight wire stylet thus could perforate the urethral wall, a most serious complication. Furthermore, catheters are usually inserted by nurses but prevailing standards of care and insurance constraints do not allow nurses to use a stylet to insert a urinary drainage catheter because of the associated risks of urethral trauma and/or perforation. It is not practicable to have a urinary catheter system that relies on a stylet for placement since nurses, who are the healthcare providers most widely relied on for catheter insertions, are not permitted to use them.

U.S. Pat. No. 4,349,029 is directed to a balloon catheter drainage system, a catheterization apparatus with a retention balloon to be expanded when the proximal end of the catheter is in the bladder. The balloon, when expanded, comprises a plurality of wings or loops that function in cooperation with at least one opening or aperture which communicates the interior bore or lumen of the catheter with the bladder so that the bladder wall cannot occlude the aperture. The design of this Patent system is such that substantially little or no residual urine remains in the bladder. With reference to FIGS. 2-6, the openings 16 are both above and below the inflatable arms of the retention element of the catheter. Furthermore, the reversibly inflatable anchoring element at the catheter end has something of a steering wheel-type shape which prevents the bladder walls from obstructing the apertures, and when inflated accomplishes the retention of the catheter within the bladder. The ring 22 is attached to the catheter shaft 17 by a plurality of spokes 23. As such, this reference Patent system includes inflatable horizontal elements as well as draining apertures, both distal and proximal to that reversibly expandable element. Second and third embodiments are reflected in FIGS. 5 and 7, where the balloon 69 has three individual loops 71 that are reversibly fillable with fluid for expansion, thereby both exposing and opening the drainage apertures 67 and 83 to accomplish the emptying of the bladder with minimal or no residual volume. In contradistinction to the present subject Patent system, this catheter system replaces the stylet with a second catheter so that the retaining part remains closed; once the retaining part is inside the bladder then the second catheter, acting as a soft stylet, is withdrawn. This system is meant to be a totally closed system to obviate the chance of catheter-related infections. Furthermore, unlike the present subject patent application, the retaining parts are inflatable. The structure of this system is complex and very expensive to manufacture.

U.S. Pat. No. 2,649,092 is directed to a catheter very similar to the present urinary catheter system. A wire or flexible member 30 is fixed to the inside proximal tip 28 and, when pulled, causes the catheter's closed end 14 to foreshorten, thereby radially displacing the "outwardly projecting portions 20" to an open configuration seen in FIG. 3-6. In contradistinction to the present subject catheter system, this reference system needs a stylet at least for its insertion. "A stylet (not shown) is inserted in tubular member 12 and its forward end is brought to bear against the rearward end of plug 24. The stylet is moved forwardly with respect to the tubular member, causing portions 20 to be extended due to their flexibility, and the catheter and stylet are inserted in a body passage to the desired location, such as into the bladder. The stylet is then removed, allowing the parts of the cathter to return to the position shown in FIG. 1." (Column 3, lines 22-32) The present invention does not use a stylet, for reasons already discussed.

U.S. Pat. No. 3,938,530 is directed to a retention-type catheter for drainage of a urinary bladder. This system is closest to the present invention insofar as its retention means consist of radially displaceable strips 11, defined by longitudinal and circumferentially spaced slits 10, which are displaced by foreshortening the catheter's proximal end. Unlike the present invention, the foreshortening is accomplished by sliding an inner secondary tube 6 within a primary tube 1, as illustrated in FIGS. 2, 3, 4. The use of a tube-within-a-tube system compromises the drainage catheter lumen and obstructs the drainage of urine. The urinary drainage system of this reference is both complex and expensive to manufacture.

U.S. Pat. No. 3,397,699 is directed at a retaining catheter having resiliently biased wing flanges, similar in certain ways to the present subject invention. The retaining flanges 4 are opened and closed by use of " . . . a relatively stiff stylet 8 . . . " (Column 3, lines 61-62) unlike the present subject catheter system. The problems and dangers associated with the use of a stylet are discussed above.

U.S. Pat. No. 4,575,371 is directed to a urinary catheter system with a retention member in the form of a reversibly expandable balloon. In this system, the expandable balloon is situated below the drainage inlet opening so that in its inflated condition a portion of the catheter tip projects past the balloon and prevents contact between the wall of the urinary bladder and catheter tip thereby minimizing infection and local tissue trauma. As may be seen in FIGS. 2-5, the retention balloon when fully expanded distends past the tip of the catheter. The embodiment of FIG. 5 reflects also that the retention balloon is bi-lobed with reversibly expandable balloon chambers 3' and 3" arranged on opposite sides of the catheter tube and which in their expanded condition project in front of the tip 2. This Patent system uses bowl-shaped balloons for retention of the urinary drainage catheter that prevents contact between the catheter tip and the bladder mucosa, thereby reducing or obviating infection and/or tissue trauma. In contradistinction to the present subject Patent system, this reference system provides for a catheter drainage hole above the retaining element, thus allowing residual urine to collect with the attendant risks of infection and bladder inflammation.

U.S. Pat. No. 3,108,595 is directed to a retention catheter system that is characterized by pre-formed mushroom-like tips that are either split or fenestrated so as to allow for the drainage of urine. This invention encompasses a catheter comprising an outer tube having one or more mushroom heads and an inner tube that is longitudinally slidable within the outer tube and serves both as a conduit for fluids as well as a means for reversibly extending the mushroom head. With reference to FIGS. 1-5 especially, the inner tube 12 can be slid longitudinally with respect to the outer tube 11 so as to cause the detent 23 to engage with a detent opening 26, at which time those portions 22 of the outer tube 11 are extended radially to provide a plurality of ring-like extensions 27 that serve to anchor or retain the catheter in the bladder, as well as to provide openings for bladder emptying. In the embodiments reflected in FIGS. and 8, drainage slots 59 are formed in the outer tube 53 and are arranged helically along the outer tube 53. Despite some similarities to the present subject Patent system, this reference system is a drainage tube with a sliding mechanism of action, designed to be inserted surgically, and inappropriate for transurethral placement.

Thus, there exists a need to replace the current indwelling urinary catheter balloon retention system with another system that is safer, less irritating and leaves essentially no residual urine.

SUMMARY OF THE INVENTION

Accordingly, it is an object of this invention to provide an indwelling elastomeric hollow tube for urinary bladder drainage that overcomes the disadvantages of the prior art.

It is a further object of this invention to provide a hollow elastomeric tube, and a method of aspirating the bladder after surgery and in certain medical conditions.

It is a further object of the this invention to provide a hollow elastomeric tube and method of irrigating the bladder in certain urological conditions.

It is a further object of the this invention to provide a hollow elastomeric tube that can have sufficient stiffness to be inserted into the bladder through the urethra without the need for a stylet.

It is an important object of the this invention to provide a hollow elastomeric tube that has means for being retained within a urinary bladder which minimize the contact area of the catheter with the bladder wall and permit complete drainage of the bladder without obstructing the outflow of urine.

It is a further object of this invention that when positioned within the bladder, the tip of the indwelling urinary drainage catheter can be reversibly opened by means that deform the catheter tip into a retaining mushroom shape in non-continuous contact with the bladder wall, and furthermore, permits all the urine to drain from the bladder.

It is still a further object of the this invention that the retaining mushroom-shaped tip of the new catheter can be opened while in the bladder by using either a control wire or a spherical or transversely positioned elongated balloon that is reversibly inflatable with less than 5 mls of water (or air or other fluid) through a valve mechanism.

BRIEF DESCRIPTION OF THE DRAWINGS

FIG. 3A is a perspective view of the urinary drainage catheter of the invention in transition between open and closed configurations.

FIG. 3B is a perspective view an open configuration of the urinary drainage catheter of the invention.

DETAILED DESCRIPTION OF THE PREFERRED EMBODIMENTS

Figure 1:
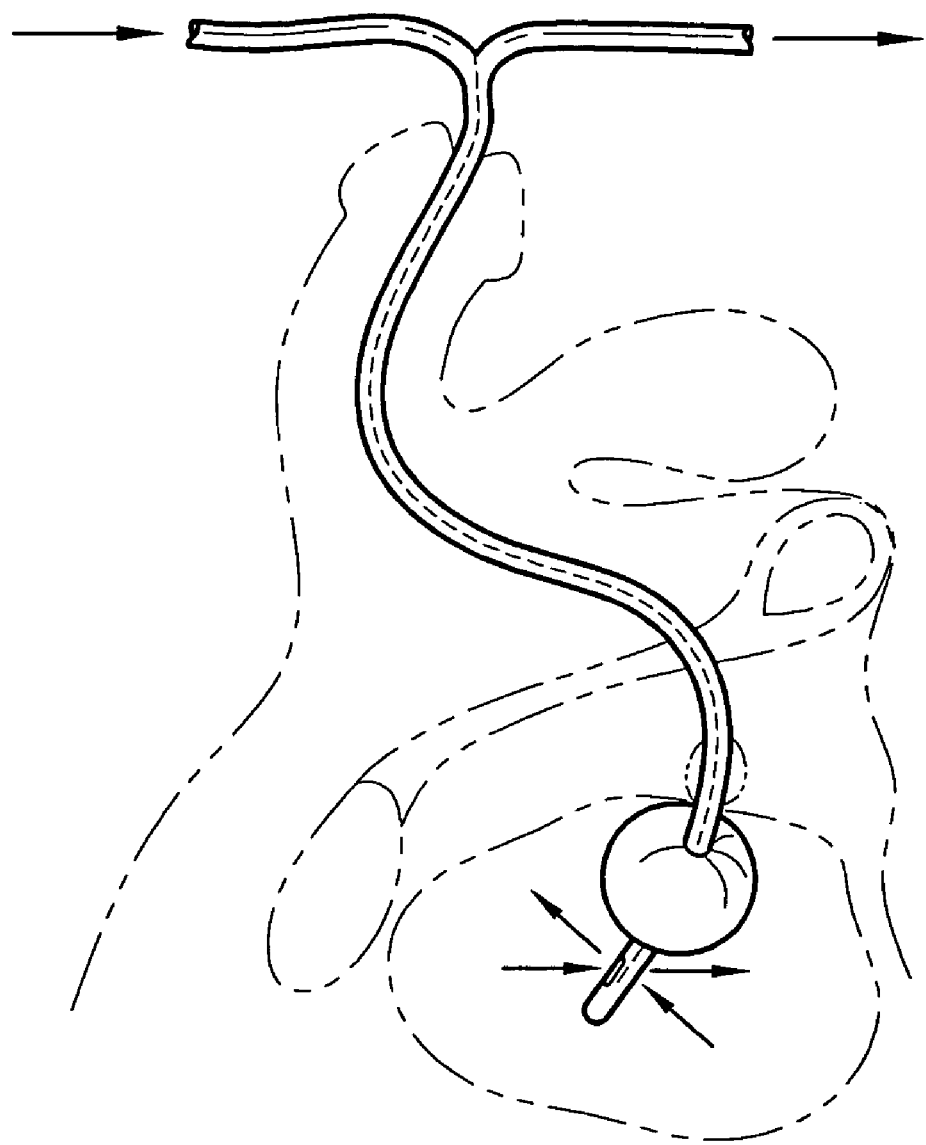
FIG. 1 is a schematic cross-sectional drawing of the prior art, an indwelling Foley catheter in situ.

Referring now to the drawings, a urinary drainage catheter of the prior art is seen in FIG. 1, illustrating a typical Foley catheter. The retaining balloon when inflated, abuts in a continuous manner against the inner bladder wall; its drainage opening is proximal to the retaining balloon and thus allows there to be residual urine pooling at the base of the bladder. The present invention provides for non-continuous contact of the retention means with the bladder, thereby reducing the area of bladder-catheter contact and the resulting bladder wall irritation. The present subject invention further provides for drainage apertures distal to the retention means thereby facilitating complete urinary drainage, that is, eliminating any residual urine and thus further reducing bladder wall irritation. Furthermore, the catheter of the present invention can be inserted into and removed from a patient without using a stylet. In addition, the catheter components for reversably activating the retention means do not substantially compromise the lumen of the drainage catheter.

A self-retaining urinary drainage catheter system, generally designated as 10 in FIGS. 2-5, which embodies the principles of the present invention is shown. Catheter 10 consists of a hollow tube 11 having a closed proximal end 12 and an open distal end 13, the catheter having a length 14. The closed proximal end 12 includes in the present embodiment, a plurality of longitudinally directed slits 15, which are circumferentially spaced. The plurality of longitudinally directed slits 15 define a plurality of flexible tube slit portions 18. The catheter system 10 is a longitudinally extending flexible tube 11 having a predetermined outer diameter 40 that allows the catheter to be placed atraumatically into the urethra and urinary bladder of a patient, with the predetermined outer diameter 40 allowing the catheter to conform to the dimensions of a normal urethra without distending the conforming urinary tract structures. Once in proper position within the urinary tract, the catheter system 10 is situated so that the flexible tube slit portions 18 are situated entirely within the urinary bladder chamber. The opened distal end 13 protrudes beyond the urethra and can accommodate the attachment of a urine collection bag (not shown), and can further be used for irrigation of the bladder so as to remove blood clots or debris.

The catheter system 10 is self-retaining by action of the retaining means, the reversible and radial displacement of the flexible tube slit portions 18 to a first configuration 16. When the catheter system 10 is in use, the closed proximal end 12 and the plurality of flexible tube slit portions 18 are located within the urinary bladder, the open distal end 13 lies outside the urethra, and the section of catheter between the closed proximal end 12 and the open distal end 13 is located within the urethra. The catheter 10 is maintained in its proper position within the bladder by the displacement of the flexible tube slit portions 18 in a reversible and radial fashion so as to form a mushroom-shaped proximal end. The first configuration 16, wherein the flexible tube slit portions 18 have been radially displaced, prevents the catheter 10 from being moved out of proper position since the first configuration 16 has a larger diameter than both the catheter's predetermined outer diameter 40 and the normal diameter of a cysto-urethral orifice. The closed proximal end 12 with the plurality of longitudinally directed slits 15 can assume a second configuration 17 as seen in FIG. 2, with a diameter substantially equal to the predetermined outer diameter 40 of the catheter system 10, thereby permitting the catheter system 10 to be inserted and/or removed from the patient's urinary bladder and urethra without trauma.

When the flexible tube slit portions 18 have been radially displaced to the first configuration 16, as seen in FIGS. 3A, 3B, 4 and 5, the spaces between the tube slit portions 18, that is, the enlarged longitudinally directed slits 15, form drainage apertures 19 both above and below the means for radially displacing the flexible tube slit portions 18. Insofar as the plurality of drainage apertures 19 extend distally to the cysto-urethral junction, the plurality of drainage apertures 19 permit substantially complete drainage of the urinary bladder without any residual volume.

Figure 2:
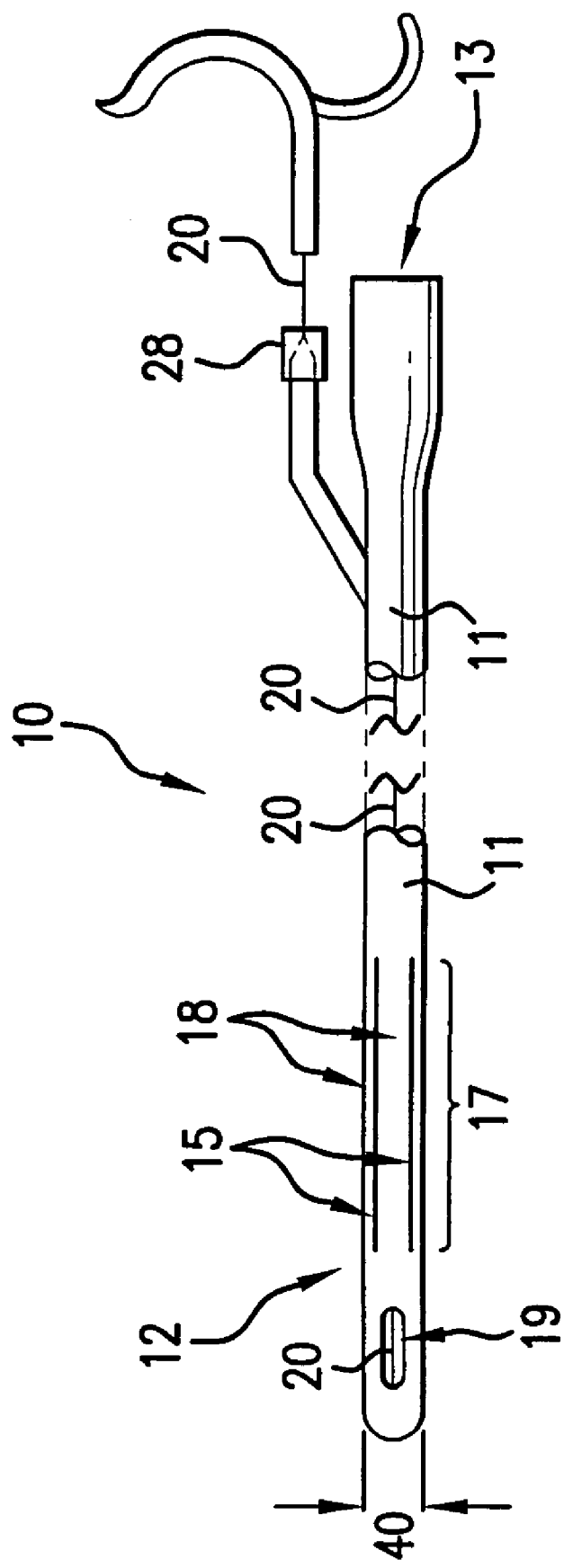
FIG. 2 is a perspective view of the urinary catheter of the invention in a closed configuration.

In order to insert the self-retaining urinary drainage catheter system 10 into the urethra and bladder of a patient, the plurality of flexible tube slit portions 18 must be in the second configuration 17 as seen in FIG. 2, that is, having substantially the same diameter as the predetermined outer diameter 40 of the catheter system 10. Once the catheter system 10 has been advanced sufficiently to place the closed proximal end 12 with the longitudinally directed slits 15 within the urinary bladder, urine within the bladder will drain into the drainage apertures 19 and flow distally through the catheter lumen 11 to the open distal end 13; the appearance of urine at the open distal end 13 gives strong presumptive evidence of the proper placement of the urinary drainage catheter system 10.

Once the catheter 10 is deemed to be in proper position, the means for reversibly and radially displacing the plurality of flexible tube slit portions 18 to the first configuration 16 is activated. By displacing the flexible tube slit portions 18 so that the proximal end 12 assumes a mushroom shape with a larger diameter than the predetermined outer diameter 40 of the catheter system 10, the flexible tube slit portions 18 abut in a non-continuous manner against the inside wall of the urinary bladder, thereby having a significantly smaller area of contact with the bladder wall than the area of contact when using the retention balloon of a typical Foley urinary catheter system seen in FIG. 1. By reducing the actual area of contact of the self-retaining means of the catheter system 10, the amount of irritation by the catheter 10 induced on the inside bladder wall, will be significantly reduced. Furthermore, because of the absence of any significant residual volume of urine in the urinary bladder, accomplished by the drainage of urine through the plurality of drainage apertures 19, there will be a further reduction in bladder irritation with which residual urine volume is associated.

In one preferred embodiment of the subject Patent system, illustrated in FIGS. 3A and 3B, the means for displacing the flexible tube slit portions 18 comprises a wire control device 20. The wire control device 20 has a first end 22 (not shown), a second end 24, a length 25 and is composed of a metal or non-metallic material with a predetermined stiffness and flexibility. In addition, the wire control device 20 has a means for reversibly locking the wire control device 28. The first end 22 of the wire control device 20 is fixedly secured to an inner wall of the closed proximal end 12 of the catheter 10. The wire control device is located within the catheter in a longitudinal and substantially coaxial relationship to the catheter 10 and its lumen. The wire control device is free to be slidably displaced by pulling on the second end 24 of the wire control device, which may have formed an easily manipulatable shape, as illustrated. The wire control device 20 has a length 25 that is greater than the length 14 of the catheter 10. By applying tension to the wire control device 20, thereby withdrawing more of the wire 20 out of the catheter 10, the closed proximal end 12 is displaced distally, as seen in FIG. 3A and 3B, thereby causing the flexible tube slit portions 18 to buckle and assume the shape as seen in the first configuration 16. By pushing the wire control device 20 in a proximal direction, the displaced flexible tube slit portions 18 are pulled straight, thereby changing the catheter system 10 configuration from the open first configuration 16 illustrated in FIG. 3B, to the closed second configuration 17 as seen in FIG. 2. In order to retain a desired configuration 16 or 17 of the catheter system 10, there is included a means 28 for reversibly locking the wire control device that is adjacent to the open distal end 13 of the catheter 10. The means 28 for reversibly locking the wire control device in a desired predetermined position may include a screw-type locking diaphragm which reversibly clamps down on the wire control device 20 so as to prevent its slidable displacement in either direction. Other locking means are well known in the art and may be substituted for the above-mentioned reversible locking means 28.

Figure 4:
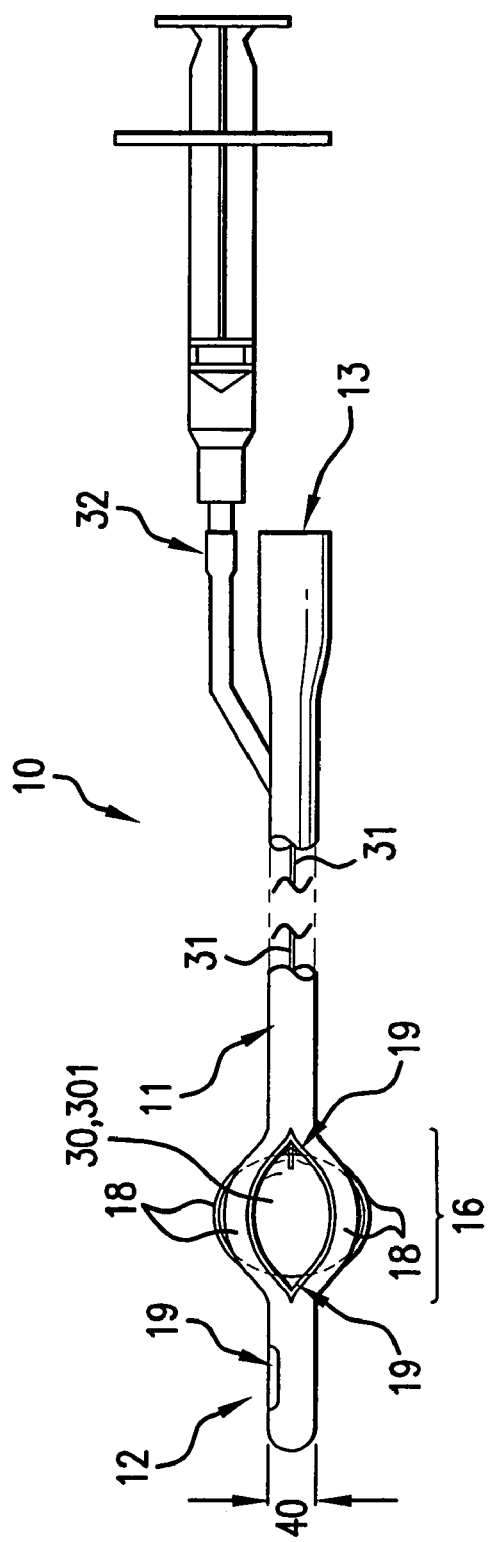
FIGS. 4 and 5 are perspective views of two preferred embodiments of the invention.
Figure 5:
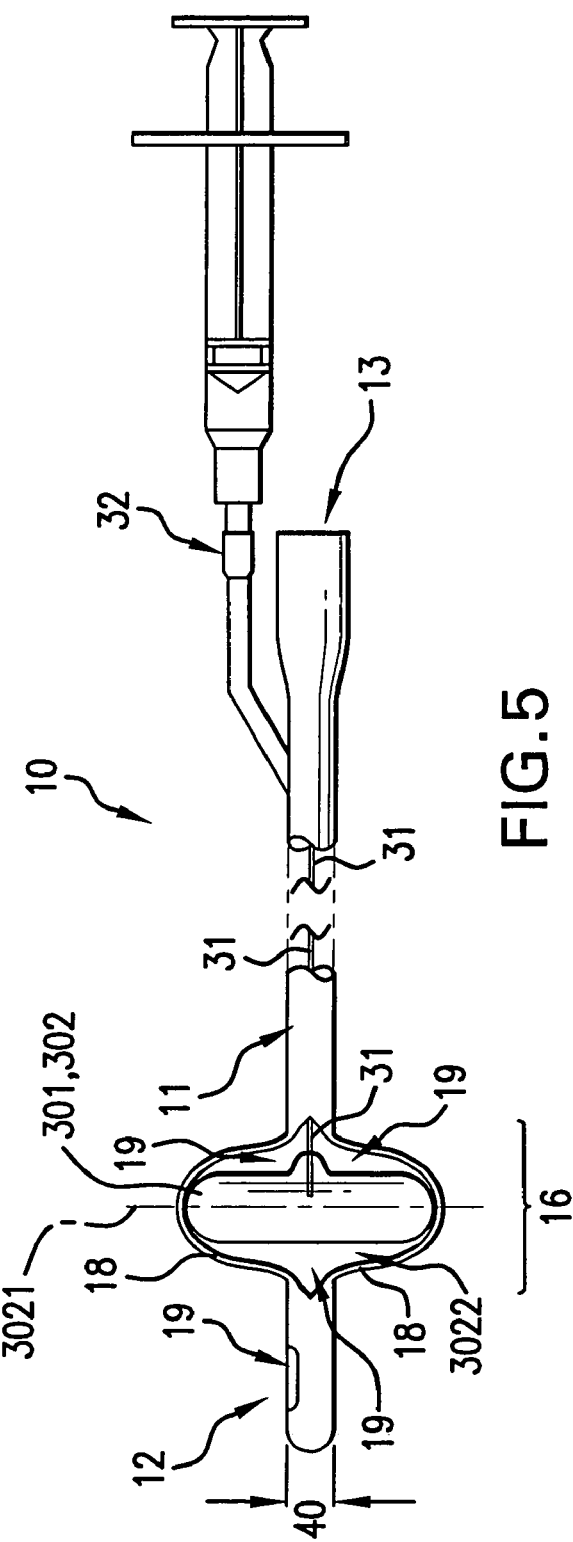

Another preferred embodiment of the self-retaining urinary drainage catheter system 10 is seen in FIGS. 4 and 5, and uses a reversibly inflatable balloon 30 as the means for displacing the flexible tube slit portions 18 to the desired first configuration 16. The reversibly inflatable balloon 30 is located centrally, in between the flexible tube slit portions 18 and longitudinally directed slits 15. A non-distensible flexible micro-catheter 31 fluidly connects the reversibly inflatable balloon 30 to an injectable valve 32 adjacent to the open distal end 13. The balloon 30 has a limited capacity and only two or three mls of fluid, preferably sterile water or saline, is needed to inflate the balloon 30 to its fully inflated configuration. The micro-catheter 31 fluidly connects at its first, proximal end to the balloon 30, and at its second, distal end to the injectable valve 32. By using a syringe or similar instrument, a suitable volume of fluid is injected through the injectable valve 32 and therethrough the flexible non-distensible micro-catheter 31 into the balloon 30. By expanding the balloon 30, the flexible tube slit portions 18 are radially displaced, thereby giving the catheter system 10 a first configuration 16 with the mushroom-shaped proximal end having a diameter significantly greater than the predetermined outer diameter of the catheter. The catheter 10 would be inserted and removed with the balloon 30 deflated, and only when deemed to be in proper position would the balloon 30 be inflated by injection of a suitable volume of fluid through the injectable valve 32, thereby giving the catheter system 10 a self-retaining configuration 16.

The reversibly inflatable balloon 30 of FIGS. 4 and 5 is any of a number of simple closed geometric shapes, defining a unitary chamber; by avoiding a plurality of connected chambers which do not form a simple closed space, the problem of blockage of one of the smaller component chambers is obviated, thereby improving the reliability of the means for displacing the proximal end 12 of the catheter system 10 to the first configuration 16. Furthermore, the process of manufacture of such a reversibly inflatable balloon is considerably simplified by avoiding multi-chamber reversibly inflatable balloon systems.

In a preferred embodiment of the urinary drainage catheter system, the reversibly inflatable balloon 30 is given a substantially spherical form 301 seen in FIG. 4. Inflation of the substantially spherical balloon 301 causes the equatorial part of the balloon sphere 301 to push in a radial direction the flexible tube slit portions 18, thereby displacing the tube slit portions 18 so as to have a larger diameter than the predetermined outer diameter of the catheter 10. With the proximal end 12 of the catheter system 10 assuming a configuration 16 characterized by a diameter greater than the predetermined outer diameter 40 of the catheter 10, the system 10 becomes self-retaining within a urinary bladder of a patient.

In another preferred embodiment depicted in FIG. 5, the reversibly inflatable balloon 30 has a simple nonspherical closed form 302, and in particular, has a cigar-like shape with a long axis 3021 and a short axis 3022; the nonspherical balloon 302 is situated between the flexible tube slit portions 18 so that its long axis 3021 is substantially perpendicular or normal to the longitudinal axis of the catheter system 10. With inflation of the nonspherical balloon 302, the balloon enlarges more in a transverse direction than a longitudinal direction so that the balloon pushes the flexible tube slit portions 18 in an outward, radial direction, causing the proximal end 12 of the catheter 10 to assume the open first configuration 16. As in the other embodiments, the catheter 10 is inserted and removed from the urinary tract of a person with the balloon deflated, and only when the catheter is in the appropriate position, with the proximal end 12 inside the urinary bladder, is the balloon inflated. The injectable valve 32 is injected with a small volume of fluid, 3 to 5 mls, whereby the injected fluid increases the pressure within the non-distensible micro-catheter 31 with which it is fluidly connected. The microcatheter further communicates the increased pressure to the nonspherical balloon 302 with which it is also fluidly connected, causing that balloon to expand against the tube slit portions 18 on which the balloon 302 abuts.

While the present invention has been shown and described in terms of a preferred embodiment thereof, it will be understood that this invention is not limited to this particular embodiment and that many changes and modifications can be made without departing from the true spirit and scope of the invention as defined in the appended claims. In addition, as used herein and in the claims, such words as "distal", "proximal", "top", "bottom", "side", and the like are used in conjunction with the drawings for purposes of clarity, and it will be appreciated that they do not limit the device to a particular orientation.

What is being claimed is:

1. A self-retaining urinary drainage catheter system, comprising:
   (a) a longitudinally extending flexible tube having a predetermined outer diameter, an open distal end and a closed proximal end, said flexible tube defining at least one lumen, said closed proximal end having a plurality of longitudinally directed slits formed through a wall of said flexible tube defining a plurality of inherently resilient flexible tube slit portions devoid of separate spring members;
   (b) a reversably and radially displaceable mechanism for displacing said plurality of flexible tube slit portions of said proximal end to a first configuration abutting in a non-continuous manner an inner surface of a urinary bladder, said first configuration of flexible tube slit portions having an outer diameter greater than said predetermined diameter of said flexible tube and defining a plurality of drainage apertures, and for displacing said plurality of flexible tube slit portions to a second configuration wherein said plurality of flexible tube slit portions has a diameter substantially equal to said predetermined outer diameter of said flexible tube, said plurality of drainage apertures being in direct fluid communication with said lumen, wherein said reversably and radially displaceable mechanism does not substantially obstruct a lumen of said catheter, and said catheter being of sufficient stiffness to be reversably insertable in a human being without using a stylet; and (c) a wire control device having a portion positionally located external and displaced from said longitudinally extending flexible tube, said wire control device having a reversible locking mechanism for locking said wire control device in a predetermined position and a portion thereof longitudinally and slidably positioned within a lumen of said longitudinally extending flexible tube, said wire control device fixedly secured at a first end to an inner surface of said closed proximal end.

2. The self-retaining urinary drainage catheter system as recited in claim 1, wherein said wire control device has a length greater than a length of said longitudinally extending flexible tube so that a second end of said wire control device protrudes through said open distal end.

3. The self-retaining urinary drainage catheter system as recited in claim 2 wherein said wire control device is composed of a metal or non-metallic material with a predetermined stiffness and flexibility.

4. A self-retaining urinary drainage catheter system, comprising:

(a) a longitudinally extending flexible tube having a predetermined outer diameter, an open distal end and a closed proximal end, said flexible tube defining at least one lumen, said closed proximal end having a plurality of longitudinally directed slits formed through a wall of said flexible tube and defining a plurality of inherently resilient flexible tube slit portions devoid of separate spring members; and, (b) a wire control device, a portion of said wire control device being substantially coaxial with and longitudinally and slidably positioned within a lumen of said longitudinally extending flexible tube, and fixedly secured at a first end to an inner surface of said closed proximal end, and having a length greater than a length of said longitudinally extending flexible tube so tat a second end protrudes through said open distal end, for reversably and radially displacing said plurality of flexible tube slit portions of said proximal end to a first configuration abutting in a non-continuous maimer an interior surface of a urinary bladder, said first configuration of said plurality of flexible tube slit portions having an outer diameter greater tan said predetermined diameter of said flexible tube and defining a plurality of drainage apertures, and displacing said plurality of flexible tube slit portions to a second configuration wherein said plurality of flexible tube slit portions has a diameter substantially equal to said predetermined outer diameter of said flexible tube, said plurality of drainage apertures being in direct fluid communication with said lumen, wherein said wire control device does not substantially obstruct a lumen of said catheter, and said catheter being of sufficient stiffness to be reversably inset-table in a human being without using a stylet.

5. The self-retaining urinary drainage catheter system as recited in claim 4, wherein said wire control device further comprises a means for reversably locking said wire control device in a predetermined position.

6. A self-retaining urinary drainage catheter system, comprising:

(a) a longitudinally extending flexible tube having a predetermined outer diameter, an open distal end and a closed proximal end, said flexible tube defining only one single lumen, said closed proximal end having a plurality of longitudinally directed slits formed through a wall of said flexible tube and defining a plurality of flexible tube slit portions; and, (b) a reversably inflatable balloon located internal said single lumen and positioned between said plurality of flexible tube slit portions and connected to an injectable valve situated adjacent to said open distal end by a flexible non-distensible micro-catheter, wherein a fluid may be reversably injected so as to expand said reversably inflatable balloon for reversably and radially displacing said plurality of flexible tube slit portions of said proximal end to a first configuration abutting in a non-continuous manner an inner surface of a urinary bladder, said first configuration of flexible tube slit portions having an outer diameter greater than said predetermined diameter of said flexible tube and defining a plurality of drainage apertures, and displacing said plurality of flexible tube slit portions to a second configuration wherein said plurality of flexible tube slit portions has a diameter substantially equal to said predetermined outer diameter of said flexible tube, said plurality of drainage apertures being in direct fluid communication with said lumen, wherein said micro-catheter does not substantially obstruct a lumen of said catheter, and said catheter being of sufficient stiffness to be reversably insertable in a human being without using a stylet.

7. The self retaining urinary drainage catheter system as recited in claim 6, wherein said reversably inflatable balloon is substantially spherical.

8. The self-retaining urinary drainage catheter system as recited in claim 6, wherein said reversably inflatable balloon defines a simple closed non-spherical chamber and has a long axis and a short axis, said long axis being of greater length than said short axis, and said reversably inflatable balloon is located wit said long axis substantially perpendicular to a longitudinal axis of said longitudinally extending flexible tube, whereby inflation of said reversably inflatable balloon displaces said plurality of flexible tube slit portions to said first configuration, and deflation of said reversably inflatable balloon displace said plurality of flexible tube slit portions to said second configuration.

* * * * *